US012636078B2

(12) United States Patent
Vu et al.

(10) Patent No.: US 12,636,078 B2
(45) Date of Patent: May 26, 2026

(54) FORCE SENSORS FOR BASKET CATHETERS

(71) Applicant: Biosense Webster (Israel) Ltd., Yokneam (IL)

(72) Inventors: Audrey Vu, Irvine, CA (US); Audrey Claire Goo, Irvine, CA (US); Robert Kato, Irvine, CA (US); Amar Patel, Irvine, CA (US); Thanh Nguyen, El Monte, CA (US); Anand Rao, Irvine, CA (US); Paul Suarez, La Crescenta, CA (US); Jacob Roseberry, Upland, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 258 days.

(21) Appl. No.: 18/500,617

(22) Filed: Nov. 2, 2023

(65) Prior Publication Data

US 2024/0189023 A1     Jun. 13, 2024

Related U.S. Application Data

(60) Provisional application No. 63/386,798, filed on Dec. 9, 2022.

(51) Int. Cl.
*A61B 18/14*          (2006.01)
*A61B 17/00*          (2006.01)
(Continued)

(52) U.S. Cl.
CPC .......... *A61B 18/1492* (2013.01); *A61B 34/20* (2016.02); *A61B 2017/00115* (2013.01); (Continued)

(58) Field of Classification Search
CPC ............... A61B 18/1492; A61B 34/20; A61B 2034/2051; A61B 2090/064; (Continued)

(56) References Cited

U.S. PATENT DOCUMENTS 4,699,147 A    10/1987   Chilson et al.
4,940,064 A     7/1990   Desai
(Continued)

FOREIGN PATENT DOCUMENTS

CN        111248993 A      6/2020
CN        111248996 A      6/2020
(Continued)

OTHER PUBLICATIONS

Extended European Search Report and Opinion dated May 7, 2024, from corresponding European Application No. 23215306.4.

*Primary Examiner* — Linda C Dvorak
*Assistant Examiner* — Abigail Bock

(57)          ABSTRACT

The disclosed technology includes a medical probe comprising a tubular shaft having a proximal end and a distal end, the tubular shaft extending along a longitudinal axis. The medical probe further comprises an expandable basket assembly coupled to the distal end of the tubular shaft. The basket assembly includes a plurality of electrodes with each electrode of the plurality of electrodes having a lumen therethrough. The basket assembly further includes a plurality of spines extending along the longitudinal axis and configured to bow radially outward from the longitudinal axis when the expandable basket assembly is transitioned from a collapsed form to an expanded form. Each spine includes a proximal and a distal end and a strut passing through the lumen of an electrode. The strut includes a
(Continued)

mechanical retainer disposed on the strut to prevent the electrode from sliding proximally or distally along a length of the spine.

17 Claims, 9 Drawing Sheets

(51) Int. Cl.

| | | |
|---|---|---|
| *A61B 18/00* | (2006.01) | |
| *A61B 34/20* | (2016.01) | |
| *A61B 90/00* | (2016.01) | |

(52) U.S. Cl.
CPC .............. *A61B 2018/00267* (2013.01); *A61B 2018/00351* (2013.01); *A61B 2018/00577* (2013.01); *A61B 2018/00613* (2013.01); *A61B 2018/1475* (2013.01); *A61B 2034/2051* (2016.02); *A61B 2090/064* (2016.02); *A61B 2562/0261* (2013.01)

(58) Field of Classification Search
CPC ........... A61B 2017/00115; A61B 2018/00267; A61B 2018/00351; A61B 2018/00577; A61B 2018/00613; A61B 2018/1475; A61B 2562/0261
See application file for complete search history.

(56) References Cited

U.S. PATENT DOCUMENTS

| | | | |
|---|---|---|---|
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |
| 5,313,943 | A | 5/1994 | Houser et al. |
| 5,324,284 | A | 6/1994 | Imran |
| 5,345,936 | A | 9/1994 | Pomeranz et al. |
| 5,365,926 | A | 11/1994 | Desai |
| 5,391,199 | A | 2/1995 | Ben-Haim |
| 5,396,887 | A | 3/1995 | Imran |
| 5,400,783 | A | 3/1995 | Pomeranz et al. |
| 5,411,025 | A | 5/1995 | Webster, Jr. |
| 5,415,166 | A | 5/1995 | Imran |
| 5,443,489 | A | 8/1995 | Ben-Haim |
| 5,456,254 | A | 10/1995 | Pietroski et al. |
| 5,465,717 | A | 11/1995 | Imran et al. |
| 5,476,495 | A | 12/1995 | Kordis et al. |
| 5,499,981 | A | 3/1996 | Kordis |
| 5,526,810 | A | 6/1996 | Wang |
| 5,546,940 | A | 8/1996 | Panescu et al. |
| 5,549,108 | A | 8/1996 | Edwards et al. |
| 5,558,073 | A | 9/1996 | Pomeranz et al. |
| 5,558,091 | A | 9/1996 | Acker et al. |
| 5,577,509 | A | 11/1996 | Panescu et al. |
| 5,595,183 | A | 1/1997 | Swanson et al. |
| 5,598,848 | A | 2/1997 | Swanson et al. |
| 5,609,157 | A | 3/1997 | Panescu et al. |
| 5,628,313 | A | 5/1997 | Webster, Jr. |
| 5,681,280 | A | 10/1997 | Rusk et al. |
| 5,722,401 | A | 3/1998 | Pietroski et al. |
| 5,722,403 | A | 3/1998 | McGee et al. |
| 5,725,525 | A | 3/1998 | Kordis |
| 5,730,128 | A | 3/1998 | Pomeranz et al. |
| 5,772,590 | A | 6/1998 | Webster, Jr. |
| 5,782,899 | A | 7/1998 | Imran |
| 5,823,189 | A | 10/1998 | Kordis |
| 5,881,727 | A | 3/1999 | Edwards |
| 5,893,847 | A | 4/1999 | Kordis |
| 5,904,680 | A | 5/1999 | Kordis et al. |
| 5,911,739 | A | 6/1999 | Kordis et al. |
| 5,928,228 | A | 7/1999 | Kordis et al. |
| 5,968,040 | A | 10/1999 | Swanson et al. |
| 6,014,579 | A | 1/2000 | Pomeranz et al. |
| 6,014,590 | A | 1/2000 | Whayne et al. |
| 6,119,030 | A | 9/2000 | Morency |
| 6,172,499 | B1 | 1/2001 | Ashe |
| 6,216,043 | B1 | 4/2001 | Swanson et al. |
| 6,216,044 | B1 | 4/2001 | Kordis |
| 6,239,724 | B1 | 5/2001 | Doron et al. |
| 6,332,089 | B1 | 12/2001 | Acker et al. |
| 6,428,537 | B1 | 8/2002 | Swanson et al. |
| 6,456,864 | B1 | 9/2002 | Swanson et al. |
| 6,484,118 | B1 | 11/2002 | Govari |
| 6,574,492 | B1 | 6/2003 | Ben-Haim et al. |
| 6,584,345 | B2 | 6/2003 | Govari |
| 6,600,948 | B2 | 7/2003 | Ben-Haim et al. |
| 6,618,612 | B1 | 9/2003 | Acker et al. |
| 6,690,963 | B2 | 2/2004 | Ben-Haim et al. |
| 6,738,655 | B1 | 5/2004 | Sen et al. |
| 6,741,878 | B2 | 5/2004 | Fuimaono et al. |
| 6,748,255 | B2 | 6/2004 | Fuimaono et al. |
| 6,780,183 | B2 | 8/2004 | Jimenez, Jr. et al. |
| 6,788,967 | B2 | 9/2004 | Ben-Haim et al. |
| 6,837,886 | B2 | 1/2005 | Collins et al. |
| 6,866,662 | B2 | 3/2005 | Fuimaono et al. |
| 6,892,091 | B1 | 5/2005 | Ben-Haim et al. |
| 6,970,730 | B2 | 11/2005 | Fuimaono et al. |
| 6,973,340 | B2 | 12/2005 | Fuimaono et al. |
| 6,980,858 | B2 | 12/2005 | Fuimaono et al. |
| 7,048,734 | B1 | 5/2006 | Fleischman et al. |
| 7,149,563 | B2 | 12/2006 | Fuimaono et al. |
| 7,255,695 | B2 | 8/2007 | Falwell et al. |
| 7,257,434 | B2 | 8/2007 | Fuimaono et al. |
| 7,399,299 | B2 | 7/2008 | Daniel et al. |
| 7,410,486 | B2 | 8/2008 | Fuimaono et al. |
| 7,522,950 | B2 | 4/2009 | Fuimaono et al. |
| 7,536,218 | B2 | 5/2009 | Govari et al. |
| RE41,334 | E | 5/2010 | Beatty et al. |
| 7,756,576 | B2 | 7/2010 | Levin |
| 7,846,157 | B2 | 12/2010 | Kozel |
| 7,848,787 | B2 | 12/2010 | Osadchy |
| 7,869,865 | B2 | 1/2011 | Govari et al. |
| 7,930,018 | B2 | 4/2011 | Harlev et al. |
| 8,007,495 | B2 | 8/2011 | McDaniel et al. |
| 8,048,063 | B2 | 11/2011 | Aeby et al. |
| 8,064,985 | B2 * | 11/2011 | Peterson ................ A61B 90/00 |
| | | | 606/130 |
| 8,103,327 | B2 | 1/2012 | Harlev et al. |
| 8,167,845 | B2 | 5/2012 | Wang et al. |
| 8,224,416 | B2 | 7/2012 | De La Rama et al. |
| 8,235,988 | B2 | 8/2012 | Davis et al. |
| 8,346,339 | B2 | 1/2013 | Kordis et al. |
| 8,435,232 | B2 | 5/2013 | Aeby et al. |
| 8,447,377 | B2 | 5/2013 | Harlev et al. |
| 8,456,182 | B2 | 6/2013 | Bar-Tal et al. |
| 8,498,686 | B2 | 7/2013 | Grunewald |
| 8,517,999 | B2 | 8/2013 | Pappone et al. |
| 8,545,490 | B2 | 10/2013 | Mihajlovic et al. |
| 8,560,086 | B2 | 10/2013 | Just et al. |
| 8,567,265 | B2 | 10/2013 | Aeby et al. |
| 8,712,550 | B2 | 4/2014 | Grunewald |
| 8,755,861 | B2 | 6/2014 | Harlev et al. |
| 8,825,130 | B2 | 9/2014 | Just et al. |
| 8,906,011 | B2 | 12/2014 | Gelbart et al. |
| 8,945,120 | B2 | 2/2015 | McDaniel et al. |
| 8,979,839 | B2 | 3/2015 | De La Rama et al. |
| 9,037,264 | B2 | 5/2015 | Just et al. |
| 9,131,980 | B2 | 9/2015 | Bloom |
| 9,204,929 | B2 | 12/2015 | Solis |
| 9,272,132 | B2 * | 3/2016 | Laufer ................ A61N 1/3601 |
| 9,277,960 | B2 | 3/2016 | Weinkam et al. |
| 9,314,208 | B1 | 4/2016 | Altmann et al. |
| 9,339,331 | B2 | 5/2016 | Tegg et al. |
| 9,486,282 | B2 | 11/2016 | Solis |
| 9,526,426 | B1 | 12/2016 | Lim |
| 9,554,718 | B2 | 1/2017 | Bar-Tal et al. |
| D782,686 | S | 3/2017 | Werneth et al. |
| 9,585,588 | B2 | 3/2017 | Marecki et al. |
| 9,597,036 | B2 | 3/2017 | Aeby et al. |
| 9,687,297 | B2 | 6/2017 | Just et al. |
| 9,693,733 | B2 | 7/2017 | Altmann et al. |
| 9,782,099 | B2 | 10/2017 | Williams et al. |

(56) References Cited

U.S. PATENT DOCUMENTS

| | | | |
|---|---|---|---|
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |
| D851,774 S | 6/2019 | Werneth et al. | |
| 10,314,505 B2 | 6/2019 | Williams et al. | |
| 10,314,507 B2 | 6/2019 | Govari et al. | |
| 10,314,648 B2 | 6/2019 | Ge et al. | |
| 10,314,649 B2 | 6/2019 | Bakos et al. | |
| 10,349,855 B2 | 7/2019 | Zeidan et al. | |
| 10,350,003 B2 | 7/2019 | Weinkam et al. | |
| 10,362,991 B2 | 7/2019 | Tran et al. | |
| 10,375,827 B2 | 8/2019 | Weinkam et al. | |
| 10,376,170 B2 | 8/2019 | Quinn et al. | |
| 10,376,221 B2 | 8/2019 | Iyun et al. | |
| 10,398,348 B2 | 9/2019 | Osadchy et al. | |
| 10,403,053 B2 | 9/2019 | Katz et al. | |
| 10,441,188 B2 | 10/2019 | Katz et al. | |
| 10,470,682 B2 | 11/2019 | Deno et al. | |
| 10,470,714 B2 | 11/2019 | Altmann et al. | |
| 10,482,198 B2 | 11/2019 | Auerbach et al. | |
| 10,492,857 B2 | 12/2019 | Guggenberger et al. | |
| 10,542,620 B2 | 1/2020 | Weinkam et al. | |
| 10,575,743 B2 | 3/2020 | Basu et al. | |
| 10,575,745 B2 | 3/2020 | Solis | |
| 10,582,871 B2 | 3/2020 | Williams et al. | |
| 10,582,894 B2 | 3/2020 | Ben Zrihem et al. | |
| 10,596,346 B2 | 3/2020 | Aeby et al. | |
| 10,602,947 B2 | 3/2020 | Govari et al. | |
| 10,617,867 B2 | 4/2020 | Mswanathan et al. | |
| 10,660,702 B2 | 5/2020 | Mswanathan et al. | |
| 10,667,753 B2 | 6/2020 | Werneth et al. | |
| 10,674,929 B2 | 6/2020 | Houben et al. | |
| 10,681,805 B2 | 6/2020 | Weinkam et al. | |
| 10,682,181 B2 | 6/2020 | Cohen et al. | |
| 10,687,892 B2 | 6/2020 | Long et al. | |
| 10,702,178 B2 | 7/2020 | Dahlen et al. | |
| 10,716,477 B2 | 7/2020 | Salvestro et al. | |
| 10,758,304 B2 | 9/2020 | Aujla | |
| 10,765,371 B2 | 9/2020 | Hayam et al. | |
| 10,772,566 B2 * | 9/2020 | Aujila | A61B 5/287 |
| 10,799,281 B2 | 10/2020 | Goertzen et al. | |
| 10,842,558 B2 | 11/2020 | Harlev et al. | |
| 10,842,561 B2 | 11/2020 | Mswanathan et al. | |
| 10,863,914 B2 | 12/2020 | Govari et al. | |
| 10,881,376 B2 | 1/2021 | Shemesh et al. | |
| 10,898,139 B2 | 1/2021 | Guta et al. | |
| 10,905,329 B2 | 2/2021 | Bar-Tal et al. | |
| 10,912,484 B2 | 2/2021 | Ziv-Ari et al. | |
| 10,918,306 B2 | 2/2021 | Govari et al. | |
| 10,939,871 B2 | 3/2021 | Altmann et al. | |
| 10,952,795 B2 | 3/2021 | Cohen et al. | |
| 10,973,426 B2 | 4/2021 | Williams et al. | |
| 10,973,461 B2 | 4/2021 | Baram et al. | |
| 10,987,045 B2 | 4/2021 | Basu et al. | |
| 11,006,902 B1 | 5/2021 | Bonyak et al. | |
| 11,040,208 B2 | 6/2021 | Govari et al. | |
| 11,045,628 B2 | 6/2021 | Beeckler et al. | |
| 11,051,877 B2 | 7/2021 | Sliwa et al. | |
| 11,109,788 B2 | 9/2021 | Rottmann et al. | |
| 11,116,435 B2 | 9/2021 | Urman et al. | |
| 11,129,574 B2 | 9/2021 | Cohen et al. | |
| 11,160,482 B2 | 11/2021 | Solis | |
| 11,164,371 B2 | 11/2021 | Yellin et al. | |
| 11,234,762 B2 * | 2/2022 | Cheng | A61L 29/08 |
| 11,241,280 B2 | 2/2022 | Ng | |
| 2004/0210121 A1 | 10/2004 | Fuimaono et al. | |
| 2006/0009689 A1 | 1/2006 | Fuimaono et al. | |
| 2006/0009690 A1 | 1/2006 | Fuimaono et al. | |
| 2006/0100669 A1 | 5/2006 | Fuimaono et al. | |
| 2007/0093806 A1 | 4/2007 | Desai et al. | |
| 2007/0276212 A1 | 11/2007 | Fuimaono et al. | |
| 2008/0234564 A1 | 9/2008 | Beatty et al. | |
| 2011/0118726 A1 | 5/2011 | De La Rama et al. | |
| 2011/0160574 A1 | 6/2011 | Harlev et al. | |
| 2011/0190625 A1 | 8/2011 | Harlev et al. | |
| 2011/0245756 A1 | 10/2011 | Arora et al. | |
| 2011/0301597 A1 | 12/2011 | McDaniel et al. | |
| 2013/0172872 A1 | 7/2013 | Subramaniam et al. | |
| 2013/0172883 A1 | 7/2013 | Lopes et al. | |
| 2013/0178850 A1 | 7/2013 | Lopes et al. | |
| 2013/0190587 A1 | 7/2013 | Lopes et al. | |
| 2013/0296852 A1 | 11/2013 | Madjarov et al. | |
| 2014/0025069 A1 | 1/2014 | Willard et al. | |
| 2014/0052118 A1 | 2/2014 | Laske et al. | |
| 2014/0180147 A1 | 6/2014 | Thakur et al. | |
| 2014/0180151 A1 | 6/2014 | Maskara et al. | |
| 2014/0180152 A1 | 6/2014 | Maskara et al. | |
| 2014/0257069 A1 | 9/2014 | Eliason et al. | |
| 2014/0276712 A1 | 9/2014 | Mallin et al. | |
| 2014/0309512 A1 | 10/2014 | Govari et al. | |
| 2015/0011991 A1 | 1/2015 | Buysman et al. | |
| 2015/0045863 A1 | 2/2015 | Litscher et al. | |
| 2015/0080693 A1 | 3/2015 | Solis | |
| 2015/0105770 A1 | 4/2015 | Amit | |
| 2015/0119878 A1 | 4/2015 | Heisel et al. | |
| 2015/0133919 A1 | 5/2015 | McDaniel et al. | |
| 2015/0208942 A1 | 7/2015 | Bar-Tal et al. | |
| 2015/0250424 A1 | 9/2015 | Govari et al. | |
| 2015/0270634 A1 | 9/2015 | Buesseler et al. | |
| 2015/0342532 A1 | 12/2015 | Basu et al. | |
| 2016/0081746 A1 | 3/2016 | Solis | |
| 2016/0113582 A1 | 4/2016 | Altmann et al. | |
| 2016/0113709 A1 | 4/2016 | Maor | |
| 2016/0183877 A1 | 6/2016 | Williams et al. | |
| 2016/0228023 A1 | 8/2016 | Govari | |
| 2016/0228062 A1 | 8/2016 | Altmann et al. | |
| 2016/0278853 A1 | 9/2016 | Ogle et al. | |
| 2016/0302858 A1 | 10/2016 | Bencini | |
| 2016/0338770 A1 | 11/2016 | Bar-Tal et al. | |
| 2017/0027638 A1 | 2/2017 | Solis | |
| 2017/0065227 A1 | 3/2017 | Marrs et al. | |
| 2017/0071543 A1 | 3/2017 | Basu et al. | |
| 2017/0071544 A1 | 3/2017 | Basu et al. | |
| 2017/0071665 A1 | 3/2017 | Solis | |
| 2017/0095173 A1 | 4/2017 | Bar-Tal et al. | |
| 2017/0100187 A1 | 4/2017 | Basu et al. | |
| 2017/0143227 A1 | 5/2017 | Marecki et al. | |
| 2017/0156790 A1 | 6/2017 | Aujla | |
| 2017/0172442 A1 | 6/2017 | Govari | |
| 2017/0185702 A1 | 6/2017 | Auerbach et al. | |
| 2017/0202515 A1 | 7/2017 | Zrihem et al. | |
| 2017/0221262 A1 | 8/2017 | Laughner et al. | |
| 2017/0224958 A1 | 8/2017 | Cummings et al. | |
| 2017/0265812 A1 | 9/2017 | Williams et al. | |
| 2017/0281031 A1 | 10/2017 | Houben et al. | |
| 2017/0281268 A1 | 10/2017 | Tran et al. | |
| 2017/0296125 A1 | 10/2017 | Altmann et al. | |
| 2017/0296251 A1 | 10/2017 | Wu et al. | |

(56)          References Cited

U.S. PATENT DOCUMENTS

| | | |
|---|---|---|
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Mswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Mswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | Desimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | | |
|---|---|---|---|
| EP | 0668740 A1 | 8/1995 | |
| EP | 0644738 B1 | 3/2000 | |
| EP | 0727183 B1 | 11/2002 | |
| EP | 0727184 B1 | 12/2002 | |
| EP | 2783651 A1 | 10/2014 | |
| EP | 2699151 B1 | 11/2015 | |
| EP | 2699152 B1 | 11/2015 | |
| EP | 2699153 B1 | 12/2015 | |
| EP | 2498706 B1 | 4/2016 | |
| EP | 2578173 B1 | 6/2017 | |
| EP | 3238645 A1 | 11/2017 | |
| EP | 2884931 B1 | 1/2018 | |
| EP | 2641555 B1 * | 6/2019 | ......... A61B 18/1492 |
| EP | 2349440 B1 | 8/2019 | |
| EP | 3318211 B1 | 12/2019 | |

(56)  References Cited

FOREIGN PATENT DOCUMENTS

| | | | |
|---|---|---|---|
| EP | 3581135 | A1 | 12/2019 |
| EP | 2736434 | B1 | 2/2020 |
| EP | 3451962 | B1 | 3/2020 |
| EP | 3972510 | A1 | 3/2022 |
| WO | 9421167 | A1 | 9/1994 |
| WO | 9421169 | A1 | 9/1994 |
| WO | 1995008943 | A2 | 4/1995 |
| WO | 9625095 | A1 | 8/1996 |
| WO | 9634560 | A1 | 11/1996 |
| WO | 0182814 | B1 | 5/2002 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014176205 | A1 | 10/2014 |
| WO | 2016019760 | A1 | 2/2016 |
| WO | 2016044687 | A1 | 3/2016 |
| WO | WO-2017041889 | A2 * | 3/2017 ........... A61B 5/6858 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020206328 | A1 | 10/2020 |

* cited by examiner

FORCE SENSORS FOR BASKET CATHETERS

CROSS REFERENCE TO RELATED APPLICATIONS

This application claims the benefit of priority under 35 U.S.C. § 119 to prior filed U.S. Provisional Patent Application No. 63/386,798, filed Dec. 9, 2022, the entire contents of which is hereby incorporated by reference as if set forth in full herein.

FIELD

The present invention relates generally to medical devices, and in particular basket catheters capable of detecting a force applied thereto.

BACKGROUND

Cardiac arrhythmias, such as atrial fibrillation (AF), occur when regions of cardiac tissue abnormally conduct electrical signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art utilize radiofrequency (RF) electrical energy to heat tissue. RF ablation can have certain risks related to thermal heating which can lead to tissue charring, burning, steam pop, phrenic nerve palsy, pulmonary vein stenosis, and esophageal fistula.

Cryoablation is an alternative approach to RF ablation that generally reduces thermal risks associated with RF ablation. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference and attached in the Appendix included in priority application No. 63/386,798.

Basket catheters are commonly used for mapping or ablating cardiac tissue. Basket catheters generally include a plurality of spines attached to the distal end of the catheter and configured to form a generally spherical shape. Some existing designs of basket catheters include a force sensor disposed between the catheter tube and the basket to sense force applied to the basket. A major limitation of these force sensors, however, is that the force sensor can only detect force applied to the basket as a whole and cannot determine the amount of force applied to each spine or in which direction the force is applied. As will be appreciated, knowing where and in what direction the force is applied to the basket can help a physician more accurately place the basket catheter and ensure sufficient contact is made between the electrodes on the basket catheter and the tissue. What is needed, therefore, are systems and methods for detecting the magnitude and direction of a force applied to various points of the basket catheter.

SUMMARY

There is provided, in accordance with an example of the disclosed technology, a medical probe comprising an insertion tube comprising a proximal end and a distal end. The insertion tube can extend along a longitudinal axis. The medical probe can comprise an expandable basket assembly coupled to the distal end of the insertion tube.

The expandable basket assembly can comprise a plurality of spines extending along the longitudinal axis and configured to bow radially outward from the longitudinal axis when the expandable basket assembly is transitioned from a collapsed form to an expanded form.

The expandable basket assembly can include a plurality of electrodes with each electrode of the plurality of electrodes being attached to a spine of the plurality of spines. The medical probe can include a force sensor attached to the expandable basket assembly and positioned distal the distal end of the insertion tube. The force sensor can be configured to detect a force applied to the expandable basket assembly.

The disclosed technology can include a controller of a medical device. The controller can be configured to receive force data from the force sensor, calculate a force applied to the expandable basket assembly based at least in part on the received force data, and output the calculated force to a connected display.

The disclosed technology can include a controller of a medical device. The controller can be configured to receive force data from multiple strain gauges, calculate a total force applied to the expandable basket assembly based at least in part on the received force data, and output the calculated force to a connected display.

The disclosed technology can include a medical system comprising a medical probe having an expandable basket assembly. The expandable basket assembly can comprise a plurality of spines extending along a longitudinal axis and configured to bow radially outward from the longitudinal axis when the expandable basket assembly is transitioned from a collapsed form to an expanded form. The expandable basket can include a plurality of electrodes. Each electrode of the plurality of electrodes can be attached to a spine of the plurality of spines. The expandable basket can comprise a force sensor attached to the expandable basket assembly. The expandable basket can comprise a controller comprising a processor and a memory in communication with the processor, the memory storing instructions configured to cause the controller to determine a change in electrical resistance of the force sensor, and determine, based on the change in electrical resistance, a force applied to the expandable basket assembly.

DETAILED DESCRIPTION

Figure 1:
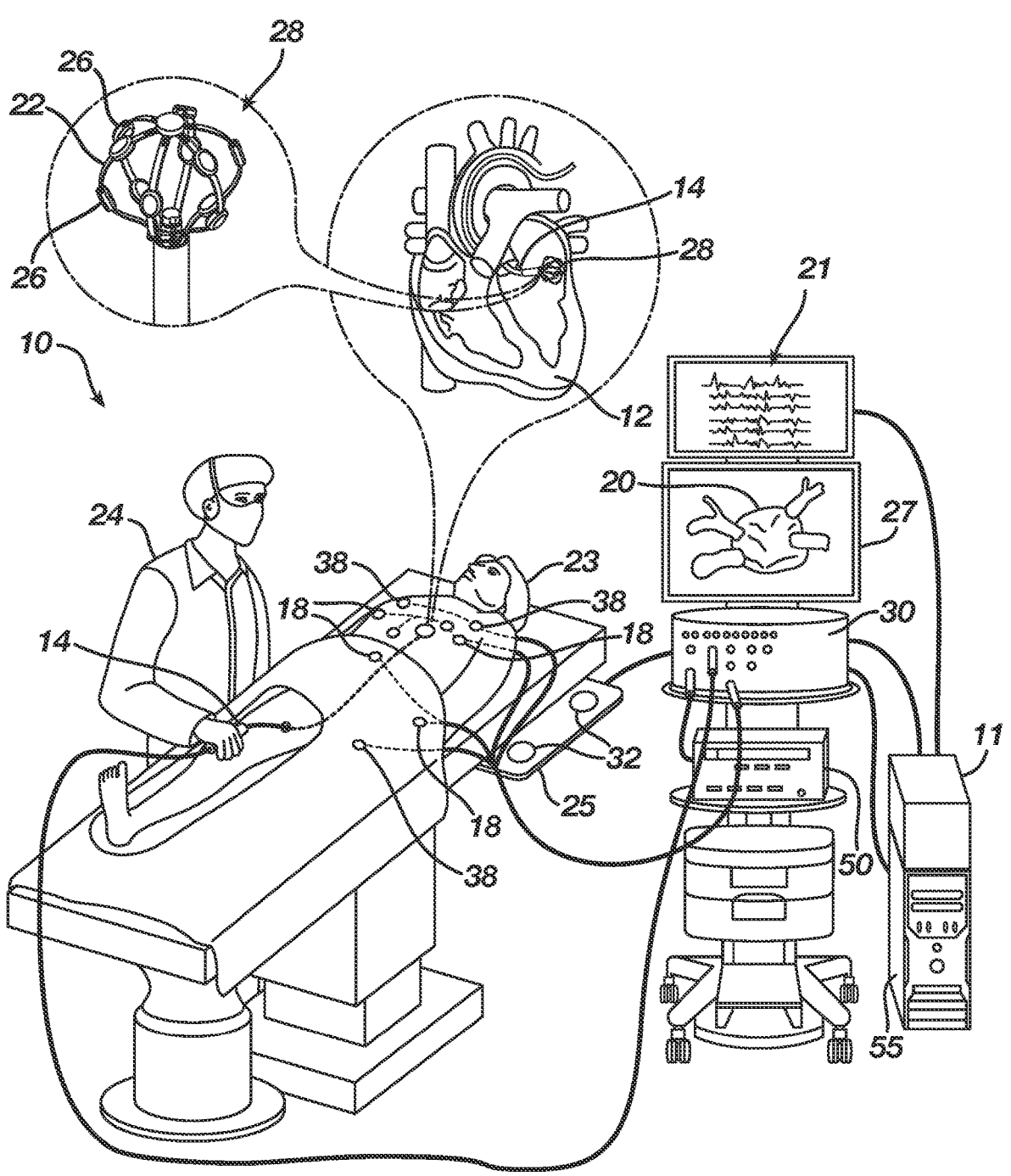
FIG. 1 is a schematic pictorial illustration of a medical system including a medical probe whose distal end includes a basket assembly with electrodes, in accordance with the disclosed technology.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%. In addition, as used herein, the terms "patient." "host." "user," and "subject" refer to any human or animal subject and are not intended to limit the systems or methods to human use, although use of the subject invention in a human patient represents a preferred embodiment. As well, the term "proximal" indicates a location closer to the operator or physician whereas "distal" indicates a location further away to the operator or physician.

As discussed herein, vasculature of a "patient." "host." "user." and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a physician, doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode having a high current density and high electric flux density is positioned at a treatment site, and a second electrode having comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal having a positive-voltage phase pulse (referred to herein as "positive phase") and a negative-voltage phase pulse (referred to herein as "negative phase"). "Monophasic pulse" refers to an electrical signal having only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape having an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating", as used herein, is defined as the maximum continuous temperature that a component can withstand during its lifetime without causing thermal damage, such as melting or thermal degradation (e.g., charring and crumbling) of the component.

Reference is made to FIG. 1 showing an example catheter-based electrophysiology mapping and ablation system 10. System 10 includes multiple catheters, which are percutaneously inserted by operator 24 through the patient's 23 vascular system into a chamber or vascular structure of a heart 12. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM is illustrated herein. Operator 24 brings a basket catheter 28 into contact with the heart wall for sensing a target site in heart 12. For ablation, operator 24 would similarly bring a distal end of an ablation catheter to a target site for ablating.

Catheter 14 is an exemplary catheter that includes one and preferably multiple electrodes 26 optionally distributed over a plurality of spines 22 forming a basket assembly 28 at a distal end and configured to sense the IEGM signals. Catheter 14 may additionally include a position sensor 29 embedded in or near the distal tip for tracking position and orientation of basket assembly 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. Real time position of basket assembly 28 of catheter 14 may be tracked based on magnetic fields generated with location pad 25 and sensed by magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091, each of which are incorporated herein by reference and attached in the Appendix included in priority application No. 63/386,798.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848, 787; 7,869,865; and 8,456,182, each of which are incorporated herein by reference and attached in the Appendix included in priority application No. 63/386,798.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof. The signals may be biphasic or monophasic.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Figure 2A:
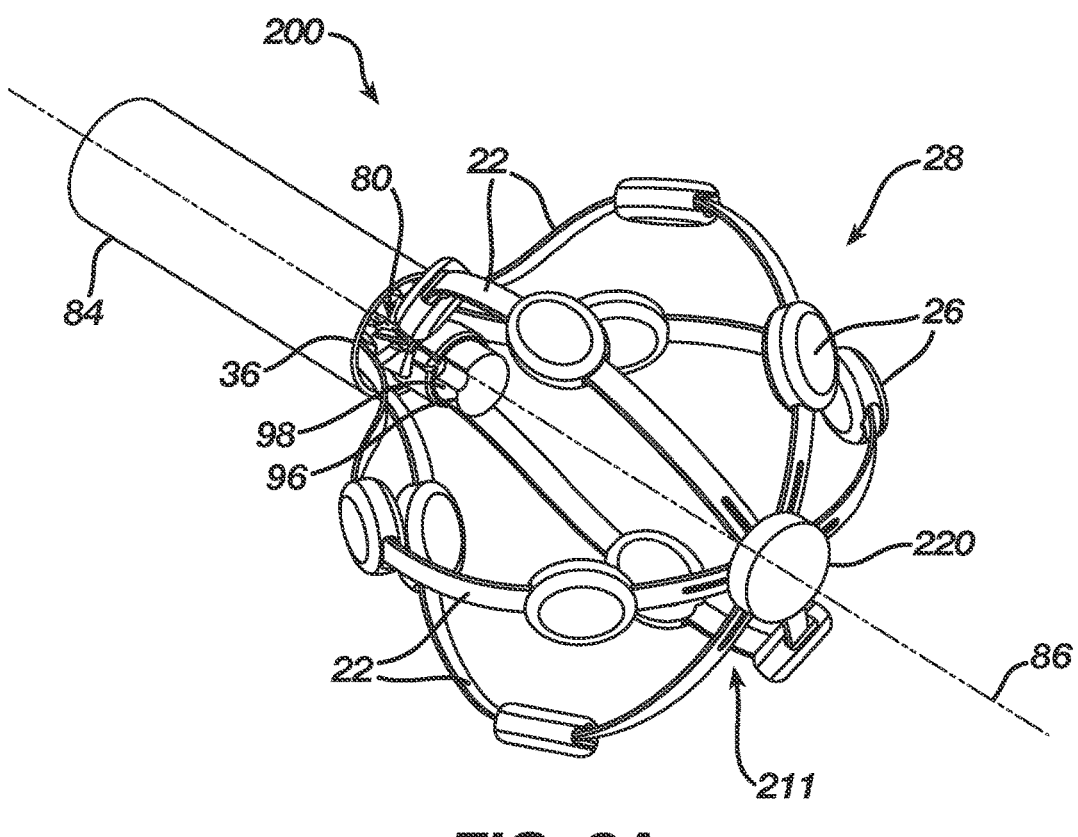
FIG. 2A is a schematic pictorial illustration showing a perspective view of a medical probe in an expanded form, in accordance with the disclosed technology.
Figure 2B:
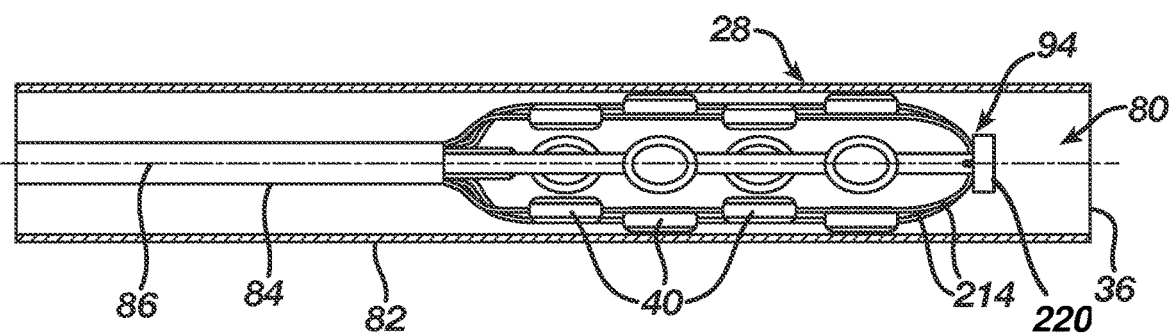
FIG. 2B is a schematic pictorial illustration showing a side view of a medical probe in a collapsed form, in accordance with the disclosed technology.

FIG. 2A is a schematic pictorial illustration showing a perspective view of a medical probe 200 having a basket assembly 28 in an expanded form when unconstrained, such as by being advanced out of a tubular shaft lumen 80 at a distal end 36 of a tubular shaft 82. FIG. 2B shows the basket assembly in a collapsed form within tubular shaft 82. In the expanded form (FIG. 2A), the spines 22 bow radially outwardly along a longitudinal axis 86 and in the collapsed form (FIG. 2B) the spines are constrained generally along the longitudinal axis 86 of tubular shaft 82.

As shown in FIG. 2A, basket assembly 28 includes a plurality of flexible spines 22 that are formed at the end of a tubular shaft 84 and are connected at both ends. During a medical procedure, operator 24 can deploy basket assembly 28 by extending tubular shaft 84 from tubular shaft 82 causing the basket assembly 28 to exit the tubular shaft 84 and transition to the expanded form. Spines 22 may have elliptical (e.g., circular) or rectangular (that may appear to be flat) cross-sections, and include a flexible, resilient material (e.g., a shape-memory alloy such as nickel-titanium, also known as Nitinol) forming a strut as will be described in greater detail herein.

In examples described herein, electrodes 40 can be configured to deliver ablation energy (RF and/or IRE) to tissue in heart 12. In addition to using electrodes 40 to deliver ablation energy, the electrodes can also be used to measure a physiological property such as local surface electrical potentials at respective locations on tissue in heart 12. The electrodes 40 can be biased such that a greater portion of the electrode 40 faces outwardly from the basket assembly 39 such that the electrodes 40 deliver a greater amount of electrical energy outwardly away from the basket assembly 28 (i.e., toward the heart 12 tissue) than inwardly toward the basket catheter 38.

Examples of materials ideally suited for forming electrodes 40 include gold, platinum, and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 12.

Basket assembly 28 can include a stem 96 that extends longitudinally from a distal end 36 of shaft 84 towards distal end 94 of basket assembly 28. The disclosed technology can include an irrigation system that delivers irrigation fluid to spray ports 98. For example, stem 96 can include multiple spray ports 98, wherein each given spray port 98 can be angled to aim delivery of the irrigation fluid to either a given electrode 40 or to tissue in heart 12. The electrodes 40 can be cooled by aiming the irrigation fluid, via spray ports 98, at the portion of the electrodes 40 on the inner side of the spines 22.

The basket assembly 28 can include a central intersection 211 at a point where the spines 22 converge near the distal end 94. The basket assembly 28 can include contact force sensor assembly 220 attached to the central intersections 211. By attaching the contact force sensor assembly 220 to the central intersection 211, the contact force sensor assembly 220 can be configured to detect a force applied to the basket assembly 28 at the distal end 94. In this way, the contact force sensor assembly 220 can be configured to more easily detect a force applied to the basket assembly 28 (e.g., when the basket assembly 28 contacts tissue).

The contact force sensor assembly 220 can be or include any suitable type of contact force sensor for the application. For example, the contact force sensor assembly 220 can be a load cell, a strain gauge, a piezoelectric sensor, a force sensing resistor, a magnetic force sensor, etc.

Figure 3:
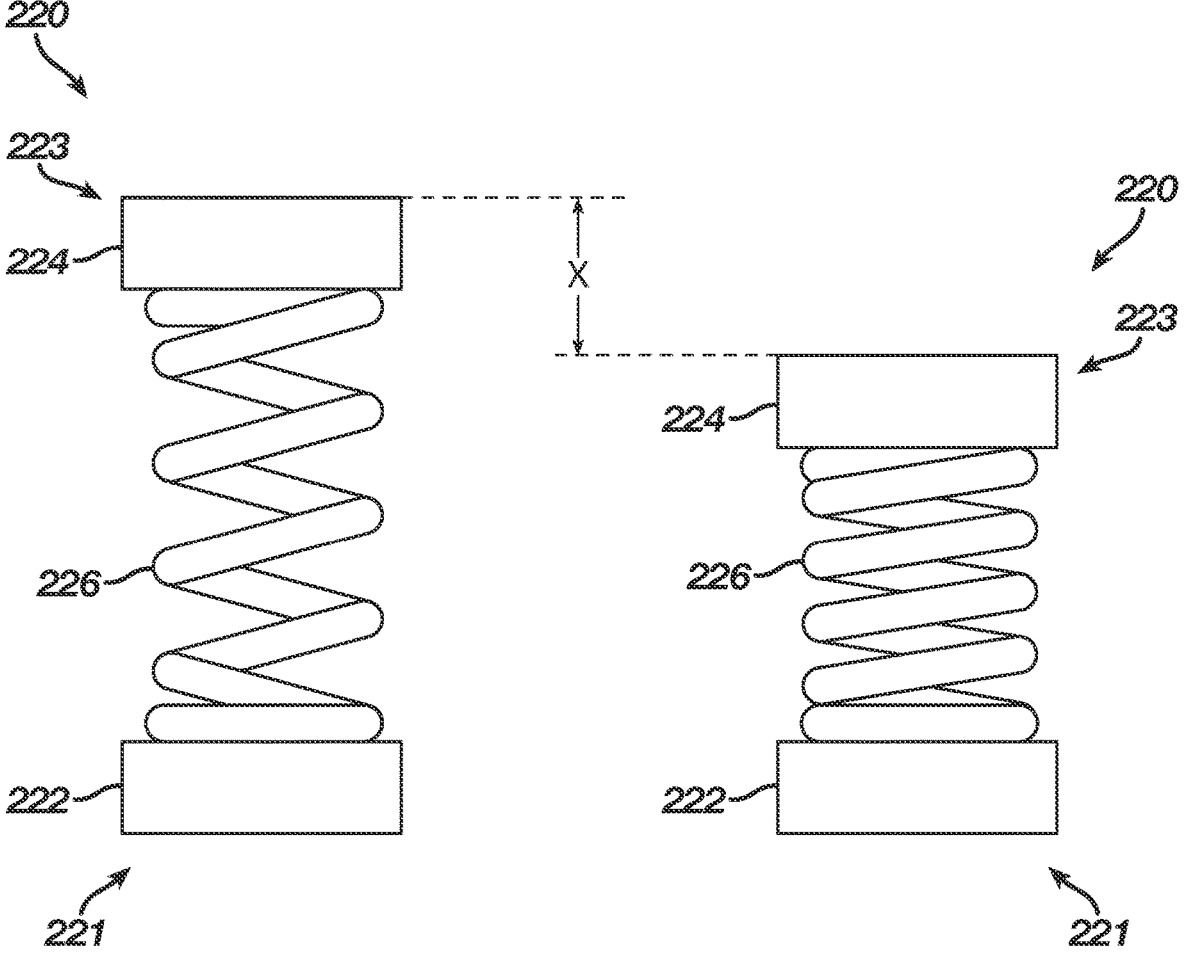
FIG. 3 is a schematic pictorial illustration of a contact force sensor showing displacement as the contact force sensor is compressed, in accordance with the disclosed technology.

As one non-limiting example illustrated in FIG. 3, the contact force sensor assembly 220 can include a proximal end 221 and a distal end 223. The proximal end 221 can house a magnetic field generator coil 222 and the distal end 223 can house a magnetic field sensor 224, or vice versa. As will be appreciated, the magnetic field generator coil 222 can be configured to generate a magnetic field while the magnetic field sensor 224 can be configured to detect the presence and magnitude of the magnetic field.

The contact force sensor assembly 220 can further include a deflection portion 226 disposed between the proximal end 221 and the distal end 223. The deflection portion 226 can be configured to deflect when a force is applied to the contact force sensor assembly 220. In other words, the deflection portion 226 can be configured to permit the proximal end 221 and the distal end 223 of the contact force sensor assembly 220 to move closer to each other when a force is applied to the contact force sensor assembly 220. To illustrate, FIG. 3 shows a change in position "X" when the deflection portion 226 is compressed as a force is applied to the contact force sensor 220. As will be appreciated, the change in position "X" increases (or be a greater distance) when the deflection portion 226 is compressed to a greater extent.

In one example, the deflection portion 226 is a spring positioned between the proximal end 221 and the distal end 223. As another example, the deflection portion 226 can comprise a helical spring formed into a body of the contact force sensor assembly 220. For example, helical cuts can be made in the body of the contact force sensor assembly 220 to form a helical spring. In this way, the body of the contact force sensor assembly 220 can itself form a spring without the need for additional components.

As will be appreciated, when the distal end 223 is moved closer to the proximal end 221 when a force is applied to the contact force sensor assembly 220, the magnetic field sensor can detect a change in the magnitude of the force of the magnetic field generated by the magnetic field generator coil. Because the spring constant K of the deflection portion 226 can be predetermined and the distance between the magnetic field generator coil and the magnetic field sensor can be detected as the distal end 223 is brought closer to the proximal end 221, the force applied to the basket catheter 28 can be determined (e.g., by using Hooke's law, or the equation $F=d*K$). Furthermore, the contact force sensor assembly 220 can receive electrical signals from, and provides electrical signals to, workstation 55, to process received signals and determine forces, e.g., sub-gram forces, exerted on the basket assembly 28.

Figure 4A:
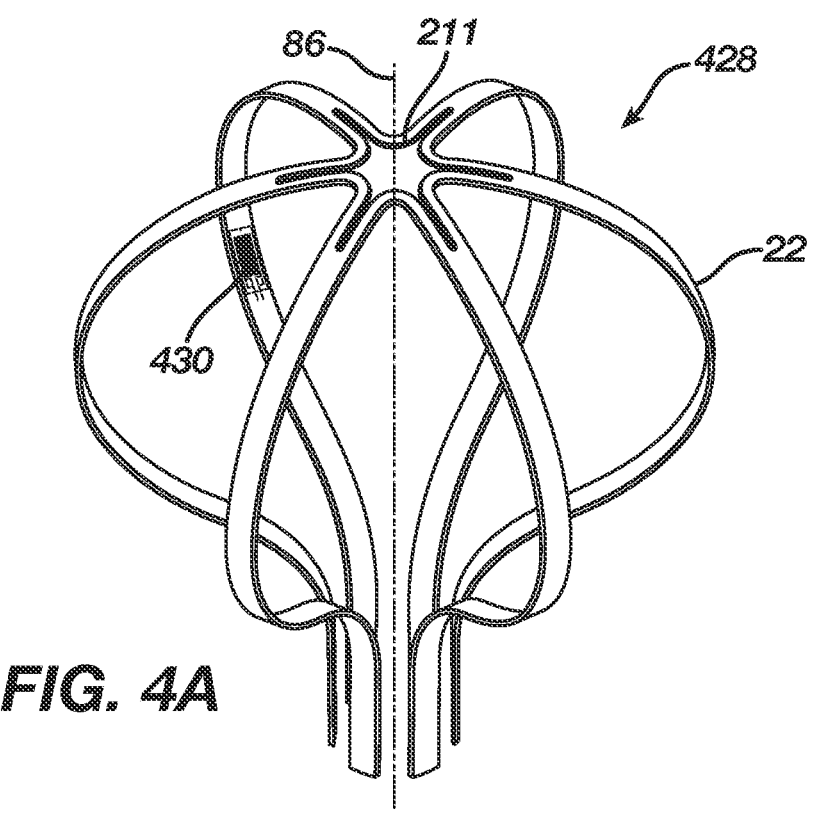
FIGS. 4A and 4B are schematic pictorial illustrations showing perspective views of a basket catheter with a force sensor attached thereto, in accordance with the disclosed technology.
Figure 4B:
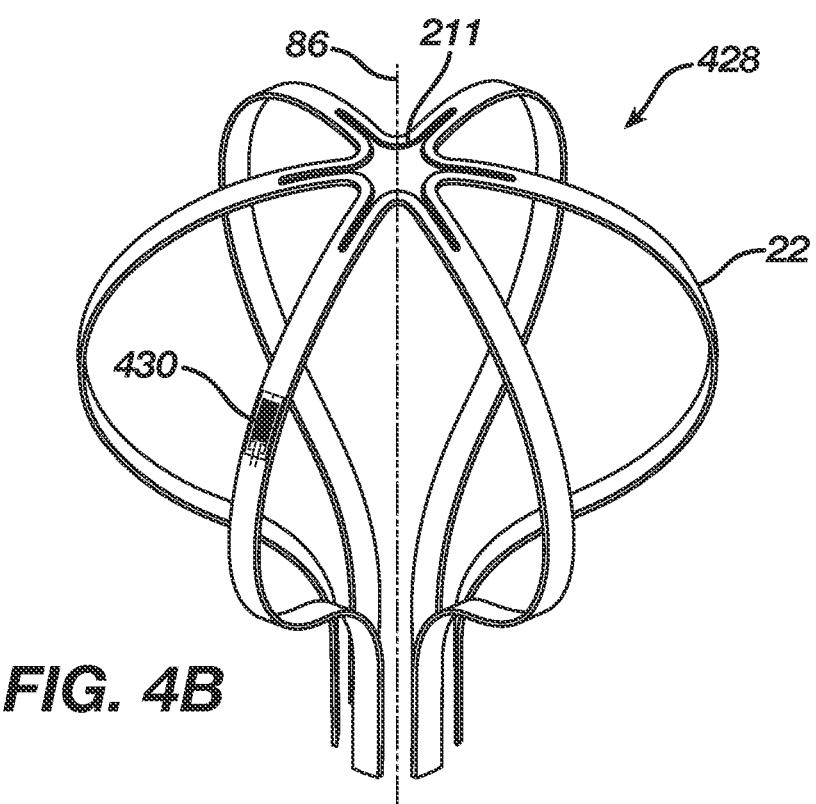

In the examples shown and described in FIGS. 4A-6B, the force sensor 430 can be a strain gauge, or other electrical resistance-based sensor, attached directly to the basket catheter 28. In this way, the disclosed technology can be better configured to detect a force applied to the basket catheter 28. To illustrate, FIGS. 4A and 4B are schematic pictorial illustrations showing perspective views of a basket catheter 428 with a force sensor 430 attached thereto, in accordance with an embodiment of the present invention. As shown in FIGS. 4A and 4B, and in contrast with existing basket catheters, the force sensor 430 can be attached to a spine 22 of the basket catheter 428. The force sensor 430 can be attached to an inwardly-facing surface (as shown in FIG. 4A) or an outwardly-facing surface (as shown in FIG. 4B) depending on the particular configuration. As will be appreciated, depending on which surface the force sensor 430 is attached to (either inwardly-facing surface or outwardly-facing surface) the force sensor 430 can detect compressive or tensile forces depending on how a force is applied to the basket catheter 428. For example, as the central intersection 211 is pushed toward the proximal end of the basket catheter 428, the spines 22 flex and an outwardly-facing surface of the spine 22 experiences tensile forces while the inwardly-facing surface of the spine 22 experiences compressive forces. One of skill in the art will appreciate that the workstation 55 can be programmed and calibrated to accurately analyze the change in signals received from the force sensor 430 depending on which surface of the spine 22 the force sensor 430 is placed.

Figure 5A:
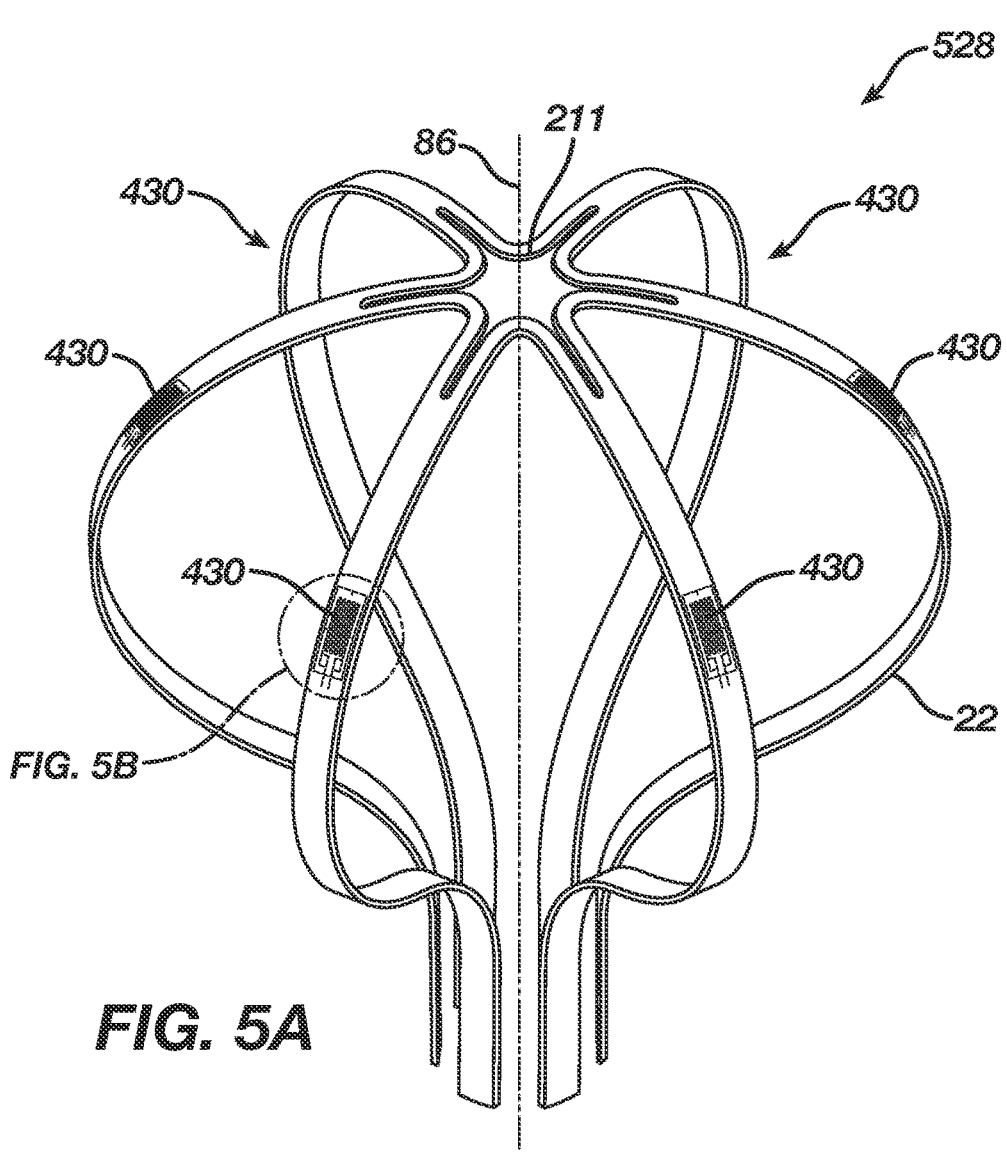
FIGS. 5A and 5B are schematic pictorial illustrations showing perspective and detail views of a basket catheter with a plurality of force sensors attached thereto, in accordance with the disclosed technology.
Figure 5B:
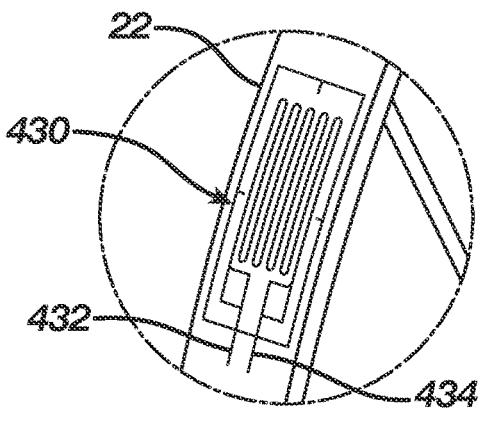

Turning now to FIGS. 5A and 5B, a basket catheter 528 can include a plurality of force sensors 430 attached to the spines 22. In particular FIG. 5A illustrates a perspective view and FIG. 5B illustrates a detail view of the basket catheter 528 with a plurality of force sensors 430 attached thereto. Although FIGS. 5A and 5B illustrate the basket catheter 528 having the force sensors 430 attached to an outwardly-facing surface of the spine 22, one of skill in the art will appreciate that the contact force sensors 430 can alternatively or additionally be attached to an inwardly-facing surface.

By including a plurality of force sensors 430 attached to the spines 22, the disclosed technology can be configured to more accurately detect a force applied to the basket catheter 528 than basket catheters 28 having only a single force sensor. For example, the workstation 55 can be configured to know which force sensor 430 is attached to which spine 22 (i.e., the workstation 55 can be programmed to correlate a signal received from a given force sensor 430 to an assigned spine 22 of the basket catheter 528). In this way, the workstation 55 can receive force signals from each of the force sensors 430 and determine the force at each spine 22 based on signals received from the assigned force sensor 430 attached to a given spine 22. In other words, the workstation 55 can be configured to detect a force applied to each spine 22 individually, determine how much force is applied to each spine 22, and determine a direction of the force applied to the basket catheter 528. For example, as a force is applied to a first side of the basket catheter 528, the degree to which each force sensor 430 is either compressed or strained can indicate where the force is originating from. To illustrate, the spine 22 nearest the location where the force is applied is more likely to compress on an outwardly-facing surface while the outwardly-facing surface of a spine 22 located further away from the location of the force is more likely to stretch as the force is applied. Thus, by correlating the type of force (compressive or tensile) and the magnitude of the force detected by a given force sensor 430 with the known position of the spine 22 on the basket catheter 528, the disclosed technology can be configured to detect the magnitude and direction of a force applied to the basket catheter 528. The disclosed technology can further determine a difference in the force applied to a first side of the basket catheter 28 and a second side of the basket catheter 28. Furthermore based on the magnitude and direction of the force applied to the basket catheter 528, the disclosed technology can be configured to determine a deflection of the basket catheter 528. As will be appreciated, knowing the deflection of the basket catheter 528 can helpful to determine whether the electrodes 26 have made sufficient contact with tissue.

For contact force sensors 430 can be sized and position as would be suitable for the particular application. For example, although the plurality of force sensors 430 are shown as having a given length and positioned on the spine 22 at the given illustrated positions, one of skill in the art will appreciate that he force sensors 430 can be larger or smaller than those shown in the figures. Furthermore, although FIGS. 5A and 5B illustrate only a single force sensor 430 attached to a single spine 22, the disclosed technology can include multiple force sensors 430 attached to a given spine 22. Furthermore, the force sensors 430 can be attached to the spine 22 using any suitable method. For example, the force sensors 430 can be attached to the spine 22 using adhesive, fasteners, crimps, etc.

Figures 6A, 6B:
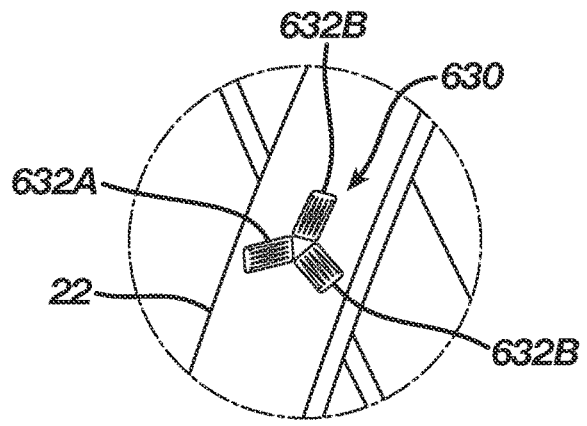
FIGS. 6A and 6B are schematic pictorial illustrations showing perspective and detail views of another basket catheter with a plurality of force sensors attached thereto, in accordance with the disclosed technology.

FIGS. 6A and 6B are schematic pictorial illustrations showing perspective and detail views of a basket catheter 628 with a plurality of force sensor arrays 630 attached thereto. All of the features just described in relation to the basket catheter 528 can be incorporated into the basket catheter 628. However, rather than having a single force sensor 430 attached to the spine 22 as shown and described with the basket catheter 528, the basket catheter 628 can have a plurality of sensor arrays 630 attached to the spines 22. The sensor arrays 630 can comprise a plurality of force sensors 632A, 632B, and 632C arranged in different directions. For example, the sensor arrays 630 can comprise three sensors arranged at 120° in relation to each other. In this way, the sensor array 630 can be used to detect a direction of force applied to the spine 22. As will be appreciated, strain gauges are typically well suited for detecting compressive or tensile forces in a given direction but generally unable to accurately detect a force in a direction transverse to the given direction. Thus, by arranging several force sensors 632A, 632B, and 632C in differing directions, the sensor array 630 can be configured to better detect a direction of a force applied to the spine 22.

The workstation 55 can be configured to receive force data from each force sensor 632A, 632B, and 632C and, based on the received data, determine a magnitude and direction of the force applied to the spine 22. Furthermore, the workstation 55 can compile all of the force data received from each for sensor 632A, 632B, and 632C from each spine 22 and determine the magnitude and direction of the force applied to the basket catheter 628. Furthermore based on the magnitude and direction of the force applied to the basket catheter 628, the disclosed technology can be configured to determine a deflection of the basket catheter 628.

Figures 7A, 7B:
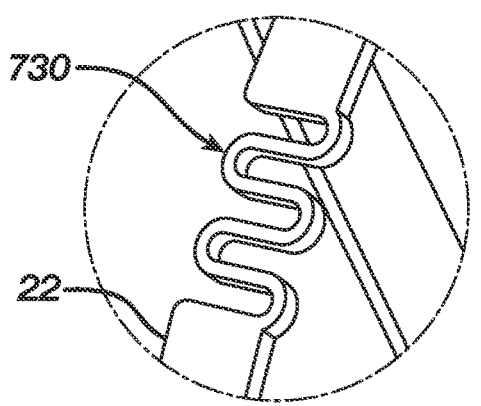
FIGS. 7A and 7B are schematic pictorial illustrations showing perspective and detail views of another basket catheter with a plurality of force sensors integrated into the spines, in accordance with the disclosed technology.

FIGS. 7A and 7B are schematic pictorial illustrations showing perspective and detail views of another basket catheter 728 with a plurality of force sensors 730 integrated into the spines 22, in accordance with an embodiment of the present invention. All of the features described in relation to the basket catheter 528 can be incorporated into the basket catheter 728. However, as shown in FIGS. 7A and 7B, the basket catheter 728 can include force sensors 730 formed into the spines 22 of the basket catheter 728. For example, the spines 22 can be made from nitinol, cobalt chromium, stainless steel, titanium, or some other biocompatible conductive material. The spine 22 can be formed to include a conductive section that has a variable electrical resistive properties as it is deformed, similar to a strain gauge. The workstation 55 can be configured to detect a change in the electrical resistance through the spine 22 due to the force sensor 730 being built directly into the spine 22. Furthermore, the workstation 55 can be configured to detect the magnitude and direction of the force applied to the basket catheter 728 as previously describe in the other examples given herein.

Figure 8A:
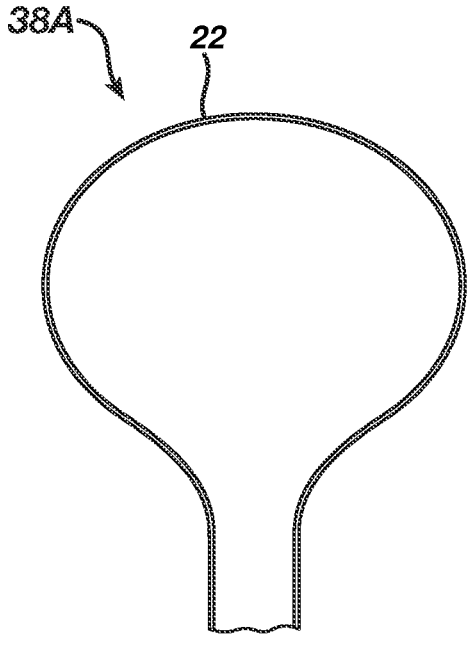
FIGS. 8A and 8B are schematic pictorial illustrations showing a side view of a spine of a given medical device, in accordance with the disclosed technology.
Figure 8B:
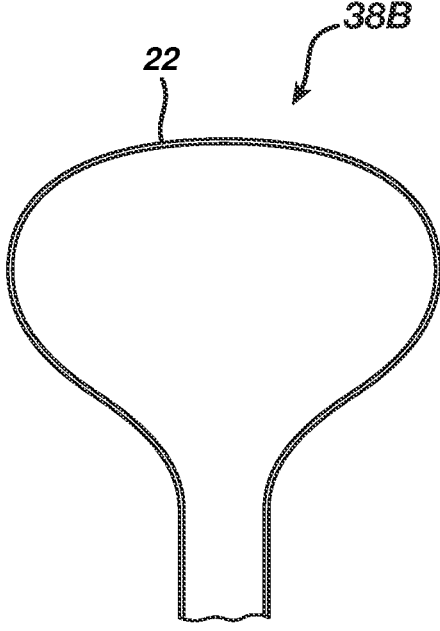

FIGS. 8A and 8B are schematic pictorial illustrations showing a side view of a spine 22 of a given basket catheter 28, in accordance with examples of the disclosed technology. As will be appreciated, the spine 22 illustrated in FIGS. 8A and 8B is a single spine 22 and can be representative of the plurality of spines 22 of the basket assembly 28 described herein. In other words, the plurality of spines 22 forming the basket assembly 28 can each be configured to form the same or similar shape when in the expanded form such that the plurality of spines 22 together form a desired shape. To illustrate, the spine 22 as shown in FIG. 8A can be configured to form an approximately circular shape when in the expanded form. Thus, when combined with other spines 22 to form the basket assembly 28, the plurality of spines 22 can be configured to form an approximately spherical shape when the basket assembly 28 is in the expanded form. As another example, the spine 22 shown in FIG. 8B can be configured to form an approximately elliptical shape when in the expanded form. Thus, when combined with other spines 22 to form the basket assembly 28, the plurality of spines 22 can be configured to form an approximately oblate-spheroid shape when the basket assembly 28 is in the expanded form. Although not every variation of shape is shown or described herein, one skilled in the art will appreciate that the spines 22 can be further configured to form other various shapes as would be suitable for the particular application.

By including spines 22 configured to form various shapes when in the expanded form, the basket assembly 28 can be configured to position the various electrodes 40 attached to the spines 22 at various locations, with each location being nearer or farther from the distal end of the flexible tubular shaft 82. For example, an electrode 40 attached to the spine 22 illustrated in FIG. 8A near the middle of the spine 22 would be farther from the distal end of the flexible tubular shaft 82 than the spine 22 illustrated in FIG. 8B when the basket assembly 28 is in the expanded form.

The workstation 55 can be calibrated to detect the magnitude and direction of the force applied to the basket catheter 28 depending on which shape the basket 28 is configured to take when fully expanded. For example, as will be appreciated, as basket catheter 28 having a more spherical shape will exhibit slightly different characteristics as it deflects when a force is applied than a basket catheter 28 having a more oblate-spheroid shape. Thus, by calibrating the workstation 55 to analyze the data received from the force sensors 430, 630, 730 dependent on the shape of the basket catheter 28, the workstation 55 can more accurately determine the magnitude and direction of the force applied to the basket catheter 28.

The disclosed technology can further include an electrically resistive jacket disposed over the spines 22 to electrically isolate the spines 22 from the electrodes 26. In this way, the electrodes 26 can be prevented from forming a short circuit to the spine 22.

Figure 9:
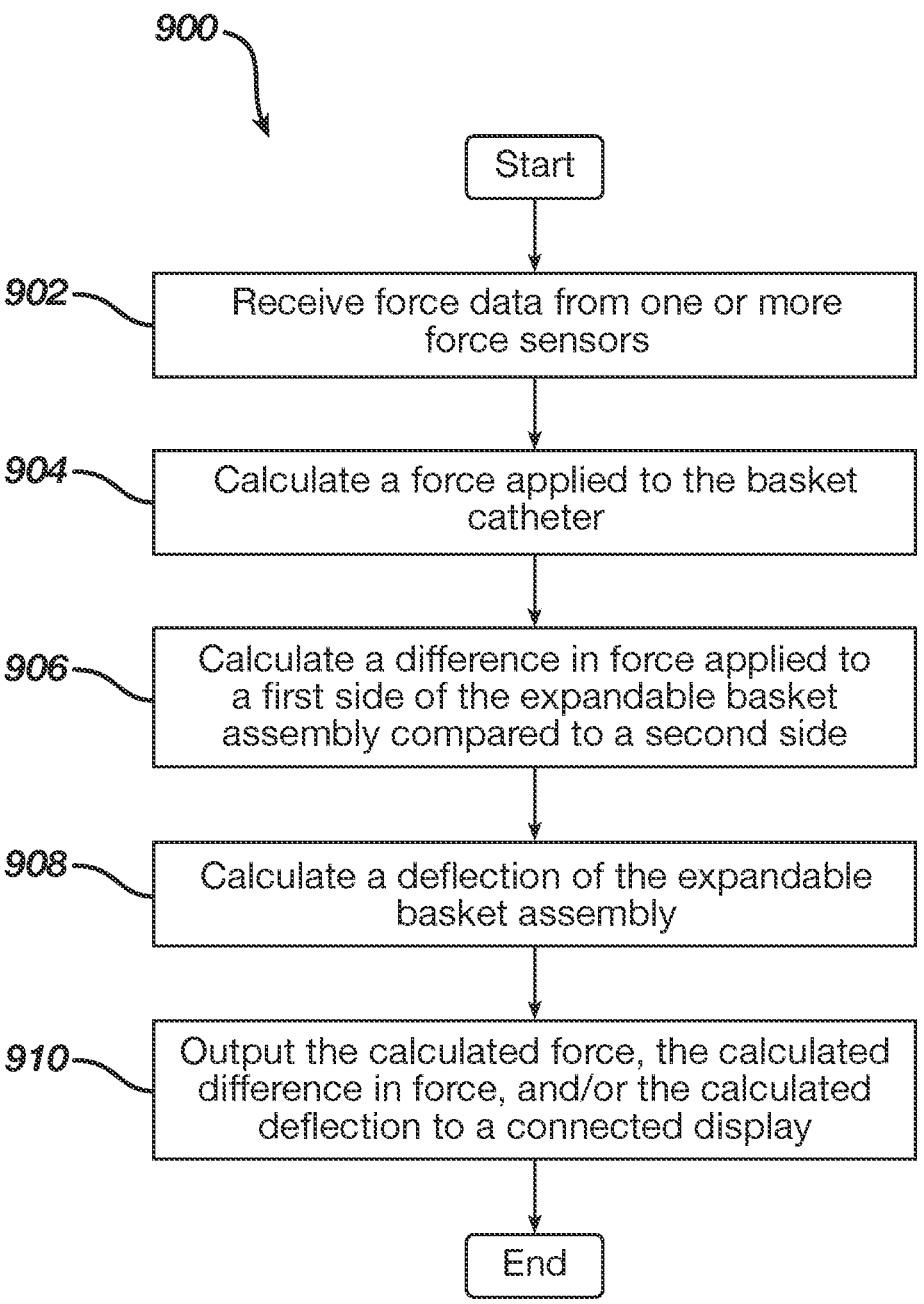
FIG. 9 is a flowchart illustrating a method of operating a medical probe having a basket assembly and a force sensor, in accordance with the disclosed technology.

FIG. 9 is a flowchart illustrating a method 900 of operating a medical probe, in accordance with an embodiment of the present invention. The method 900 can include aligning receiving 902 force data from one or more force sensors (e.g., force sensors 430, 630, 730) attached to a spine (e.g., spine 22) of a basket catheter (e.g., basket catheter 28, 428, 528, 628, 728). The method 900 can include determining 904 a force applied to the basket catheter. For example, the method 900 can include determining a magnitude and a direction of a force applied to the basket catheter. The method 900 can further include determining 906 a difference in force applied to a first side of the basket catheter compared to a second side of the basket catheter. The method can include determining 908 a deflection of the basket catheter and outputting 910 the calculated force, the calculated difference in force, and/or the calculated deflection. Outputting the calculated force, the calculated difference in force, and/or the calculated deflection can include outputting the foregoing to a connected display and/or to a processor for further processing. Further processing, for example, can include correlating the calculated force, the calculated difference in force, and/or the calculated deflection to an image of a basket catheter to illustrate a deflection of the basket catheter.

As will be appreciated by one skilled in the art, the method 900 can include any of the various features of the disclosed technology described herein and can be varied depending on the particular configuration. That is, the method 900 can be varied to include any of the features described in relation to basket catheter 28, basket catheter 428, basket catheter 528, basket catheter 628, and/or basket catheter 728.

The disclosed technology described herein can be further understood according to the following clauses:

Clause 1: A medical probe, comprising: an insertion tube having a proximal end and a distal end, the insertion tube extending along a longitudinal axis; and an expandable basket assembly coupled to the distal end of the insertion tube, the expandable basket assembly comprising: a plurality of spines extending along the longitudinal axis and configured to bow radially outward from the longitudinal axis when the expandable basket assembly is transitioned from a collapsed form to an expanded form; a plurality of electrodes, each electrode of the plurality of electrodes being attached to a spine of the plurality of spines; and a force sensor attached to the expandable basket assembly and positioned distal the distal end of the insertion tube, the force sensor configured to detect a force applied to the expandable basket assembly.

Clause 2: The medical probe according to Clause 1, wherein the force sensor is configured to detect a difference in force applied to a first side of the expandable basket assembly compared to a second side of the expandable basket assembly.

Clause 3: The medical probe according to Clause 2, wherein the force sensor is further configured to detect the force applied to each spine of the plurality of spines.

Clause 4: The medical probe according to Clause 1, wherein the expandable basket assembly comprises a proximal end and a distal end, and wherein the force sensor is attached to the distal end of the expandable basket assembly.

Clause 5: The medical probe according to Clause 4, wherein the force sensor is attached to a spine intersection of the expandable basket assembly.

Clause 6: The medical probe according to Clause 4 or 5, wherein the force sensor comprises a strain gauge attached to a distal end of the expandable basket assembly.

Clause 7: The medical probe according to Clause 4 or 5, wherein the force sensor comprises: a magnetic field generator coil configured to generate a magnetic field; a magnetic field sensor, the magnetic field sensor being configured to detect a change in a magnitude of the magnetic field generated by the magnetic field generator; and a spring disposed between the generator coil and the sensor.

Clause 8: The medical probe according to Clause 1, wherein the force sensor comprises at least one strain gauge.

Clause 9: The medical probe according to Clause 8, wherein the at least one strain gauge comprises three strain gauges disposed in different directions on each spine so that a direction of a force applied to the spine on which the strain gauges are disposed thereon can be determined.

Clause 10: The medical probe according to Clause 8, wherein the strain gauge is attached to a spine of the plurality of spines.

Clause 11: The medical probe according to Clause 10, wherein the strain gauge is attached to an inwardly-facing surface of the spine, the inwardly-facing surface of the spine facing toward an inner portion of the expandable basket assembly.

Clause 12: The medical probe according to Clause 10, wherein the strain gauge is attached to an outwardly-facing surface of the spine, the outwardly-facing surface of the spine facing outwardly from the expandable basket assembly.

Clause 13: The medical probe according to Clause 10 further comprising a plurality of strain gauges, wherein each strain gauge of the plurality of strain gauges is attached to a respective spine of the plurality of spines.

Clause 14: The medical probe according to Clause 1, wherein at least one spine of the plurality of spines forms a strain gauge such that the at least one spine of the plurality of spines is configured change a resistance of an electrical current passing through the at least one spine of the plurality of spines when there is a change in force applied to the at least one spine of the plurality of spines.

Clause 15: The medical probe according to Clause 14, wherein each spine of the plurality of spines forms a strain gauge.

Clause 16: The medical probe according to Clauses 1-15, wherein each spine of the plurality of spines is made from nitinol.

Clause 17: The medical probe according to any of Clauses 1-15, wherein each spine of the plurality of spines comprises a material selected from a group consisting of nitinol, cobalt chromium, stainless steel, titanium.

Clause 18: The medical probe according to any of Clauses 1-17, wherein the plurality of spines is configured to form an approximately spherically-shaped basket assembly when in the expanded form.

Clause 19: The medical probe according to any of Clauses 1-17, wherein the plurality of spines is configured form an approximately oblate-spheroid basket assembly when in the expanded form.

Clause 20: The medical probe according to any of Clauses 1-19, further comprising spray ports configured to deliver an irrigation fluid to the plurality of electrodes.

Clause 21: The medical probe according to any of Clauses 1-20, further comprising a plurality of electrically insulative jackets each disposed between a respective spine of the plurality of spines and a respective electrode of the plurality of electrodes, thereby electrically isolating the plurality of electrodes from the plurality of spines.

Clause 22: A controller of a medical device, the controller configured to: receive force data from the force sensor of the medical probe of Clause 1; calculate a force applied to the expandable basket assembly based at least in part on the received force data; and output the calculated force to a connected display.

Clause 23: The controller of the medical device of Clause 22, wherein the controller is further configured to: calculate a difference in force applied to a first side of the expandable basket assembly compared to a second side of the expandable basket assembly based at least in part on the received force data; and output the calculated difference in force to the connected display.

Clause 24: The controller of the medical device of Clause 23, wherein the controller is further configured to: calculate a deflection of the expandable basket assembly based at least in part on the calculated difference in force; and output the calculated deflection to the connected display.

Clause 25: A controller of a medical device, the controller configured to: receive force data from each strain gauge of the medical probe of Clause 13; calculate a total force applied to the expandable basket assembly based at least in part on the received force data; and output the calculated force to a connected display.

Clause 26: The controller of the medical device of Clause 25, wherein the controller is further configured to: calculate an individual force applied to each spine of the plurality of spines; and output the calculated individual forces to the connected display.

Clause 27: The controller of the medical device of Clause 26, wherein the controller is further configured to: calculate a deflection of the basket assembly based at least in part on the calculated individual forces; and output the calculated deflection to the connected display.

Clause 28: A medical system comprising: a medical probe having an expandable basket assembly, the expandable basket assembly comprising: a plurality of spines extending along a longitudinal axis and configured to bow radially outward from the longitudinal axis when the expandable basket assembly is transitioned from a collapsed form to an expanded form; a plurality of electrodes, each electrode of the plurality of electrodes being attached to a spine of the plurality of spines; and a force sensor attached to the expandable basket assembly; and a controller comprising a processor and a memory in communication with the processor, the memory storing instructions configured to cause the controller to: determine a change in resistance of the force sensor; and determine, based on the change in resistance, a force applied to the expandable basket assembly.

Clause 29: The medical system according to Clause 28, wherein the force sensor is a strain gauge.

Clause 30: The medical system according to Clause 29, wherein the strain gauge is disposed at a distal end of the expandable basket assembly.

Clause 31: The medical system according to Clause 29, wherein the strain gauge is disposed on a spine of the plurality of spines.

Clause 32: The medical system according to Clause 31, wherein the strain gauge is attached to an inwardly-facing surface of the spine, the inwardly-facing surface of the spine facing toward an inner portion of the expandable basket assembly.

Clause 33: The medical system according to Clause 31, wherein the strain gauge is attached to an outwardly-facing surface of the spine, the outwardly-facing surface of the spine facing outwardly from the expandable basket assembly.

Clause 34: The medical system according to Clause 29 further comprising a plurality of strain gauges, wherein each strain gauge of the plurality of strain gauges is attached to a respective spine of the plurality of spines.

Clause 35: The medical system according to Clause 29, wherein at least one spine of the plurality of spines forms a strain gauge such that the at least one spine of the plurality of spines is configured change a resistance of an electrical current passing through the at least one spine of the plurality of spines when there is a change in force applied to the at least one spine of the plurality of spines.

Clause 36: The medical system according to Clause 35, wherein each spine of the plurality of spines forms a strain gauge.

Clause 37: The medical system according to Clauses 28-36, wherein each spine of the plurality of spines is made from nitinol.

Clause 38: The medical system according to any of Clauses 28-36, wherein each spine of the plurality of spines comprises a material selected from a group consisting of nitinol, cobalt chromium, stainless steel, titanium.

Clause 39: The medical system according to any of Clauses 28-38, wherein the plurality of spines is configured to form an approximately spherically-shaped basket assembly when in the expanded form.

Clause 40: The medical system according to any of Clauses 28-38, wherein the plurality of spines is configured form an approximately oblate-spheroid basket assembly when in the expanded form.

Clause 41: The medical system according to any of Clauses 28-40, further comprising spray ports configured to deliver an irrigation fluid to the plurality of electrodes.

Clause 42: The medical system according to any of Clauses 28-41, further comprising a plurality of electrically insulative jackets each disposed between a respective spine of the plurality of spines and a respective electrode of the plurality of electrodes, thereby electrically isolating the plurality of electrodes from the plurality of spines.

The embodiments described above are cited by way of example, and the present invention is not limited by what has been particularly shown and described hereinabove. Rather, the scope of the invention includes both combinations and sub combinations of the various features described hereinabove, as well as variations and modifications thereof which would occur to persons skilled in the art upon reading the foregoing description and which are not disclosed in the prior art.

What is claimed is:

1. A medical system, comprising:
an insertion tube having a proximal end and a distal end, the insertion tube extending along a longitudinal axis; and
an expandable basket assembly coupled to the distal end of the insertion tube, the expandable basket assembly comprising:
a plurality of spines extending along the longitudinal axis and configured to bow radially outward from the longitudinal axis when the expandable basket assembly is transitioned from a collapsed form to an expanded form;
a plurality of electrodes, each electrode of the plurality of electrodes being attached to a spine of the plurality of spines; and
a force sensor attached to the expandable basket assembly and positioned distal the distal end of the insertion tube, the force sensor configured to detect a force applied to the expandable basket assembly; and
a controller configured to:
receive force data from the force sensor;
calculate a difference in force applied to a first side of the expandable basket assembly compared to a second side of the expandable basket assembly based at least in part on the received force data; and
output the calculated difference in force to a display.

2. The medical system according to claim 1, wherein the expandable basket assembly comprises a proximal end and a distal end, and
wherein the force sensor is attached to the distal end of the expandable basket assembly.

3. The medical system according to claim 2, wherein the force sensor is attached to a spine intersection of the expandable basket assembly.

4. The medical system according to claim 2, wherein the force sensor comprises a strain gauge attached to a distal end of the expandable basket assembly.

5. The medical system according to claim 2, wherein the force sensor comprises:
a magnetic field generator coil configured to generate a magnetic field;
a magnetic field sensor, the magnetic field sensor being configured to detect a change in a magnitude of the magnetic field generated by the magnetic field generator; and
a spring disposed between the generator coil and the sensor.

6. The medical system according to claim 1, wherein the force sensor comprises at least one strain gauge.

7. The medical system according to claim 6, wherein the at least one strain gauge comprises three strain gauges disposed in different directions on each spine so that a direction of a force applied to the spine on which the strain gauges are disposed thereon can be determined.

8. The medical system according to claim 6, wherein the strain gauge is attached to a spine of the plurality of spines.

9. The medical system according to claim 8, wherein the strain gauge is attached to an inwardly-facing surface of the spine, the inwardly-facing surface of the spine facing toward an inner portion of the expandable basket assembly.

10. The medical system according to claim 8, wherein the strain gauge is attached to an outwardly-facing surface of the spine, the outwardly-facing surface of the spine facing outwardly from the expandable basket assembly.

11. The medical system according to claim 8 further comprising a plurality of strain gauges,
wherein each strain gauge of the plurality of strain gauges is attached to a respective spine of the plurality of spines.

12. The medical system according to claim 1, wherein at least one spine of the plurality of spines forms a strain gauge such that the at least one spine of the plurality of spines is configured change a resistance of an electrical current passing through the at least one spine of the plurality of spines when there is a change in force applied to the at least one spine of the plurality of spines.

13. The medical system according to claim 1, the controller configured to:
calculate a force applied to the expandable basket assembly based at least in part on the received force data; and
output the calculated force to a display.

14. The medical system according to claim 1, wherein the controller is further configured to:
calculate a deflection of the expandable basket assembly based at least in part on the calculated difference in force; and
output the calculated deflection to the display.

15. A medical system comprising:
a medical probe having an expandable basket assembly, the expandable basket assembly comprising:
a plurality of spines extending along a longitudinal axis and configured to bow radially outward from the longitudinal axis when the expandable basket assembly is transitioned from a collapsed form to an expanded form;
a plurality of electrodes, each electrode of the plurality of electrodes being attached to a spine of the plurality of spines; and
a force sensor attached to the expandable basket assembly; and
a controller comprising one or more processors and a memory in communication with the one or more processors, the memory storing instructions configured to cause the controller to:
receive force data from the force sensor;
calculate a difference in force applied to a first side of the expandable basket assembly compared to a second side of the expandable basket assembly based at least in part on the received force data; and
output the calculated difference in force to a display.

16. The medical system according to claim 15, wherein the force sensor comprises a strain gauge.

17. The medical system according to claim 16 further comprising a plurality of strain gauges,
wherein each strain gauge of the plurality of strain gauges is attached to a respective spine of the plurality of spines.

* * * * *